United States Patent
Hampton et al.

(10) Patent No.: US 6,445,941 B1
(45) Date of Patent: Sep. 3, 2002

(54) METHOD AND APPARATUS FOR NON-INVASIVELY DETECTING, MEASURING, AND RECORDING ELECTROCARDIOGRAMS IN CONSCIOUS ANIMALS

(76) Inventors: Thomas G. Hampton, 224 Calumet St., Boston, MA (US) 02120; Jose M. Otero, 500 Memorial Dr., Cambridge, MA (US) 02139

( * ) Notice: Subject to any disclaimer, the term of this patent is extended or adjusted under 35 U.S.C. 154(b) by 0 days.

(21) Appl. No.: 09/523,770

(22) Filed: Mar. 11, 2000

Related U.S. Application Data

(60) Provisional application No. 60/123,857, filed on Mar. 12, 1999, and provisional application No. 60/165,519, filed on Nov. 15, 1999.

(51) Int. Cl.$^7$ .................................................. A61B 5/04
(52) U.S. Cl. ........................................ 600/393; 600/372
(58) Field of Search .............................. 600/372, 386, 600/393, 395, 509, 11

(56) References Cited

U.S. PATENT DOCUMENTS

| | | | |
|---|---|---|---|
| 4,219,027 A | * | 8/1980 | Lund .......................... 600/372 |
| 4,250,888 A | * | 2/1981 | Grosskopf ................... 600/372 |
| 4,344,440 A | * | 8/1982 | Aaby et al. .................. 600/372 |

* cited by examiner

Primary Examiner—Linda C. M. Dvorak
Assistant Examiner—David M. Ruddy
(74) Attorney, Agent, or Firm—Lahive & Cockfield, LLP; Giulio DeConti; Sean D. Detweiler

(57) ABSTRACT

A novel method and apparatus for obtaining the electrocardiogram (ECG) in small conscious animals, such as mice, without the need to anesthetize or instrument the animal, are described. The apparatus includes an array of conductive pads, embedded in a platform, the pads sized and spaced to advance contact between an animal's paws and the pads as the animal freely moves upon the platform. Electrical circuitry to the pads is configured to sense the parings of pads and paws that render an interpretable ECG signal and to activate or deactivate recording of the signals. The apparatus is suspended above a surface to minimize the range of motion of the animal without physical restraint. The method and apparatus of the present invention are intended to replace the use of anesthetics or invasive procedures to obtain ECGs in mice, to limit the range of motion of mice without physical restraint or harnessing, and to advance a common level of animal activity for animal-to-animal comparisons of cardiovascular function.

35 Claims, 7 Drawing Sheets

| ECG Index | Wild-type (n=7) | PLB-KO (n=8) | *P* value |
|---|---|---|---|
| HR (bpm) | 624 + 34 | 733 + 24 | 0.020 |
| PR (ms) | 28.5 + 1.3 | 24.4 + 1.2 | 0.035 |
| QT (ms) | 14.1 + 0.9 | 12.2 + 0.3 | 0.007 |
| PQ (ms) | 24.1 + 1.2 | 20.3 + 1.3 | 0.050 |
| QRS (ms) | 9.3 + 0.4 | 8.1 + 0.2 | 0.014 |
| ST (ms) | 4.8 + 0.2 | 4.1 + 0.1 | 0.003 |

*FIG. 7*

METHOD AND APPARATUS FOR NON-INVASIVELY DETECTING, MEASURING, AND RECORDING ELECTROCARDIOGRAMS IN CONSCIOUS ANIMALS

CROSS REFERENCE TO RELATED APPLICATIONS

This application claims the benefit of U.S. Provisional Application No. 60/123,857, filed Mar. 12, 1999 entitled "Electrophysiological Signal Acquisition System" and U.S. Provisional Application No. 60/165,519, filed Nov. 15, 1999 entitled "Apparatus for Minimizing Motion of a Mouse and Other Small Mammals While Enabling Recording the Electrocardiogram and Other Physiological Measurements".

REFERENCES CITED

U.S. Patent Documents

U.S. Pat. No. 4,250,888 February 1981 Heartbeat monitoring process and device; Nappholz, et. al.

U.S. Pat. No. 5,111,869 May 1992 Implantable ambulatory electrocardiogram monitor; Grosskopf

Other Publications

Vetterlein, F, et al. "Method for measurement of heart rate in awake, non-instrumented small animals", American Journal of Physiology 247(16), pp. H1010–H1012, 1984.

www.indusinstruments.com; description of ECG monitoring device for mice with built-in ECG electrode contact pads.

TECHNICAL FIELD

The present invention relates generally to physiologically monitoring devices for animals, and is particularly directed to noninvasively recording of the cardiac electrocardiogram in conscious mice. The invention will be specifically disclosed in connection with an apparatus and method that permits uninhibited movement of rodents on a platform that limits the range of motion of the animal without constraint, and conductive pads arranged to promote automatic recording of the electrocardiogram of the mouse while freely moving on said platform.

BACKGROUND OF THE INVENTION

Animals in general, and rodents in particular, have long been used in biomedical research of human disease conditions and therapeutics. The mouse is probably the most extensively used animal in biomedical research. Mice are the animal of choice for experimentation because of their small size, short reproductive cycle, and breadth of knowledge known about mice and their genetics. As completion of the human and mouse genome mapping projects near completion, non-invasive measurement of physiological parameters in large numbers of mice should become desirable. For example, measurement of heart rate, heart rate variability, and electrocardiographic indices have, for nearly a century, provided clinicians with important diagnostic tools; these data in mice may provide valuable information regarding the roles of genes and drugs in human disease.

A problem exists with currently available techniques for recording the electrocardiogram in mice. Currently available techniques require anesthetic and/or surgical implantation of radiotransmitters. Anesthesia, however, may depress cardiovascular function, and recovery after radio transmitter implantation is nearly 3 weeks. Neither anesthetic nor surgery is amenable to studying large populations of mice. In studying or understanding disease processes, it is almost always preferable to examine a subject in a conscious and relaxed state. If large numbers of conscious mice could be examined, then investigators might be able to determine more precisely gender, strain, and age dependent effects. Moreover, the effects of genes or drugs can be interpreted more precisely if the confounding effects of anesthetic and surgery are eliminated.

One popular method of recording ECGs in conscious mice is surgical implantation of radiotransmitters into the belly of the mouse. However, the implants weigh nearly 2 gms and impose a significant strain on the animal's physiology. In mice, it takes nearly 3 weeks for the animal to recover from surgery. While the method does permit collection of ECG data in conscious free moving mice once it recovers from the original surgical insult, the surgery and recovery period does not advance recording ECGs in large quantities of mice.

Various literatures describe the use of radiotelemetry for recording the ECG in small rodents, including mice. One perceived benefit of the radiotransmitter implants is that the device does enable the recording of the ECG in the conscious mouse. However, these publications also point out the anesthesia and surgical procedures and the lengthy recovery period.

Vetterlein et al. (Am J Physiol 247:H1010–H1012; 1984) describe a method for measurement of heart rate in awake, noninstrumented rats. In their paper, they describe detection of the heart rate in a rat by placing the rat in a small enclosure within a plastic 4-sided cage with built-in metal plates. A manual switch was activated to record heart rate when it was determined that a front leg and a back leg were touching two pads.

There is yet need for an apparatus and method to noninvasively monitor and record ECGs in large quantities of conscious mice that do not entail anesthetic, surgery, or confinement.

SUMMARY OF THE INVENTION

Accordingly, we developed a novel method and apparatus for obtaining ECGs in conscious mice by placing the animal on a platform embedded with paw-sized ECG pads connected to signal recording equipment. The cardiac electric potential of the animal is detected via the paws of the animal and relayed to an amplifier and signal acquisition equipment. This technique is much less traumatic to the mouse, requires no anesthesia or surgery, attachment of wires to the animal or confinement of the animal, and promotes rapid screening of large numbers of mice.

It is one object of the invention to provide a device that measures the ECG in conscious mice by way of an array of paw-sized conductive pads arranged in a platform upon which a mouse is free to move.

Applicant has recognized that most mice will not attempt to alight from a raised platform. Were the array of conductive pads arranged on a platform simply placed on a plane of a larger surface, the animal will in most instances transpose itself from the device to the neighboring surface. With the pads embedded in an elevated platform, however, the animal is least likely to depart said platform. Accordingly, it is another object of the invention to provide an elevated platform configured to limit the range of motion of the animal, yet not restrain the animal, which enables measurement of the ECG and other physiological parameters in conscious mice.

Applicant has recognized the need for evaluating large numbers of mice. Mice have highly developed sense of smell. Moreover, they defecate and urinate often. Accordingly, it is desirable to enable the device of the present invention to record ECGs in numerous mice by providing a new platform for each mouse. Hence, the device of the present invention provides a disposable conductive-pad embedded platform such that ECGs for each mouse are obtained via a new and fresh platform.

As such, a further aim of the present invention is the provision for rapid and facile attachment and detachment of the conductive-pad embedded platform into a housing that provides electrical contact between the platform and the ECG recording equipment.

Applicant has also recognized that mice seldom stand still and, as such, it is unlikely that the contact between paws and conductive pads will be continuous. Rather than record electrical data that is not representative of the animal's electrocardiogram, it is desirable to cease recording when the animal's paws are not in cooperation with the pads and to activate recording when the animal's paws are in contact with the pads. One object of the invention is to provide means for selectively recording the ECG when 3 of the animals' paws are in contact with 3 conductive pads. It is yet another object of the present invention to automate measurement and recording of the ECG dependent on cooperation between the animal's paws and the conductive pads.

Noninvasive measurement of other physiological variables in mice, as well as other means for obtaining those measurements, is becoming increasingly valuable to investigators using mouse models. For example, nuclear magnetic resonance (NMR) imaging is increasingly valuable because of its ability to non-invasively image the internal organs of the mouse. However, the animal is typically anesthetized to keep the animal from moving, and introduction of metallic instrumentation may confound data measurements inside the magnet, or test environment. To date, no one has described NMR imaging of the conscious mouse, and the ECG in the unconscious mouse is used to gate the acquisition of the images. Accordingly, in another aspect of the present invention, none of the components in the invention are metallic, and the electrical conduits comprise of ionic solution-filled tubing linking the animal and ECG platform positioned within the test environment to the recording equipment positioned external to the test environment. As such, one embodiment of the invention we describe enables ECG-gated NMR imaging of conscious mice.

Mice exhibit behavior suggestive of stress if they are placed in a receptacle of small volume and enclosing; walls. Moreover, mice will attempt to climb walls and may succeed if the walls are insufficiently high or if made from a material that the mouse is able to sufficiently grip with its paws. Accordingly, the device of the present invention does not include enclosing walls and so does not substantially invoke behavior suggestive of confinement nor give the animal a vertically arranged object or surface to inspect or climb. Rather, the present invention provides a recording platform that maximizes the likelihood of achieving effective quiescence of the animal, while enabling the recording of electrocardiographic signals from the conscious, unrestrained animal.

Additional objects, advantages, and other novel features of the invention will be set forth in part in the description that follows, and in part, will become apparent to those skilled in the art upon examination of the following or may be learned with the practice of the invention. The objects and advantages of the invention may be realized and obtained by means of the instrumentalities and combinations particularly pointed out in the appended claims.

BRIEF DESCRIPTION OF THE DRAWINGS

FIG. 7 is a summary table of results of interpretation of ECG waveforms obtained in 7 control (wild-type) and 8 knock-out (phospholamban-knock-out [PLB-KO]) mice using the present invention.

BRIEF DESCRIPTION OF THE PREFERRED EMBODIMENTS

Figure 1:
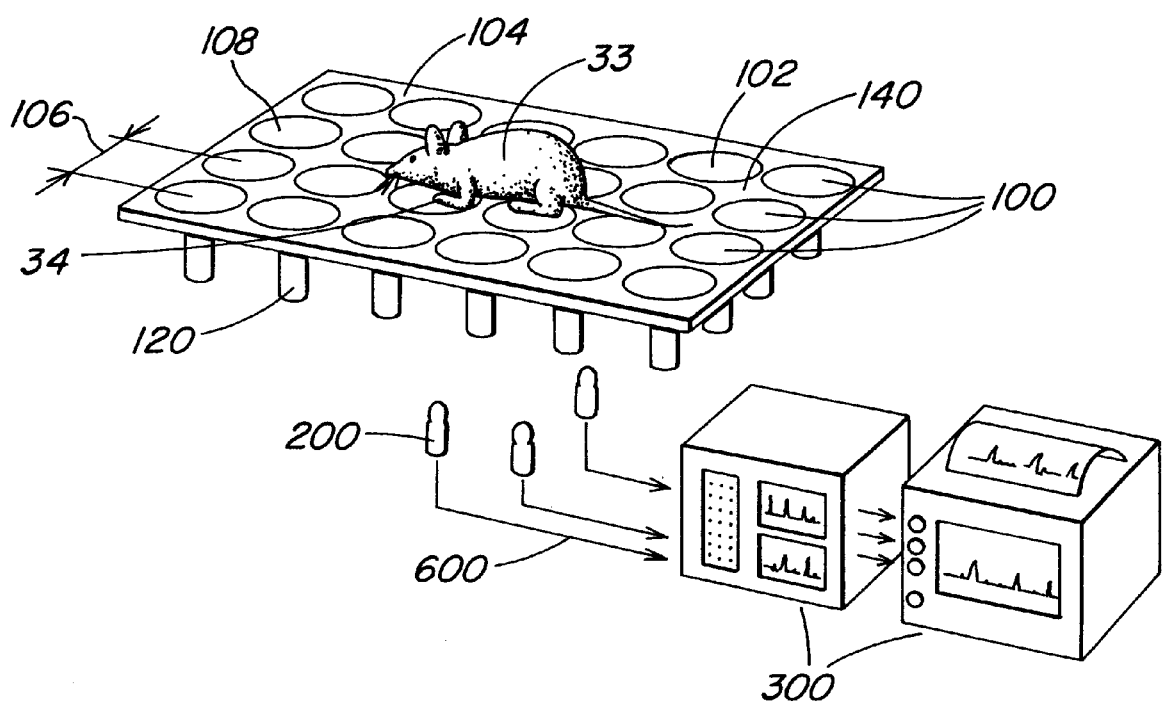
FIG. 1 is a perspective view of an array of conductive pads upon which a conscious rodent is ambulating, conductive pads in electrical contact with signal recording equipment in accordance with the present invention.

Referring now to FIG. 1, the preferred embodiment consists of an array 100 of conductive pads 102 embedded in a nonconductive platform 104 upon which a mouse 33 is free to move. The spacing 106 of the pads is such that if one paw 34 is on one pad 102 then it is likely that at least two of the other paws of the mouse are also positioned on pads. In other words, the preferred spacing of the pads is similar to the nominal spacing existent between paws of the average mouse when the mouse is resting on all fours. Moreover, the size 108 of the pads 102 is such that there is sufficient spacing between pads to prevent electrical communication between the pads. The pads are not so small that the contact between the paws and the pads is insufficient. The pads may be treated with a conductive gel on their exposed surface to improve electrical contact between them and the paws. The electrical terminations 120 of the pads 102 protrude from the underside of the pads and platform 104 to where electrical contacts 200 to the recording equipment 300 are established. The preferred terminations 120 of the pads are of highly electrically conductive material, such as AgCl, and are shaped to provide excellent electrical connection when secured to circuitry means 600 to complete the electrical circuit to the recording equipment 300. The nonconductive platform 104 is sized to allow enough area for a mouse 33 to comfortably rest on the platform, which is approximately 6 square inches, or 2"×3". A platform of greater surface area would accommodate a greater sized array of conductive pads and a greater area for ambulation. The preferred embodiment of the platform 104 also comprises a liquid absorbing material 140 on the surface of the platform in the spaces between the conductive pads. The preferred liquid-absorbing means 140 is a thin sheet of filter paper that matches the outline of the platform and comprises openings that match the shape and spacing of the pads, with adhesive means to secure the filter paper to the platform.

Figure 2:
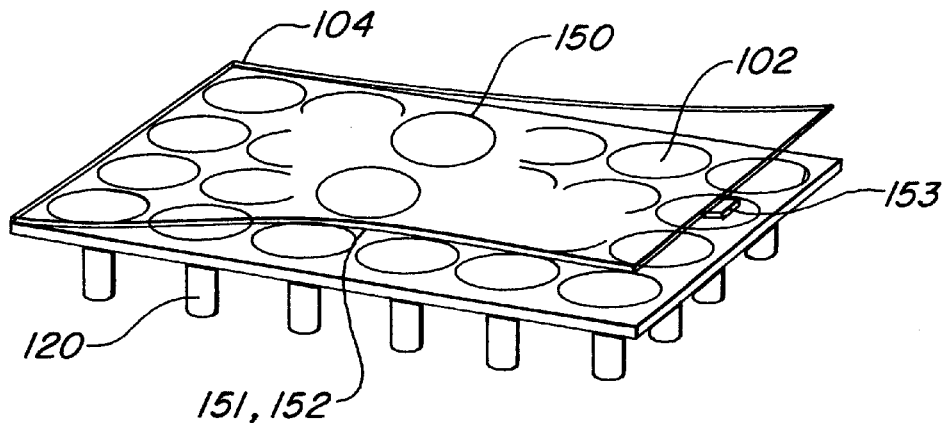
FIG. 2 is a perspective view of a disposable platform, including a detachable protective sheath removed prior to implementing the platform.

As shown in FIG. 2, the preferred embodiment of the ECG platform is designed to be disposable. Accordingly, a sheath 150 of removable plastic is fitted over the top surface of the platform 104, the underside 151 of the sheath of which is coated with a light epoxy 152 only at the perimeter of the sheath to detachably engage the perimeter of the platform. Additional length 153 of plastic sheath at one end provides a grasping means for detaching the sheath from the platform just prior to use of the platform for its intended purpose.

Figure 3:
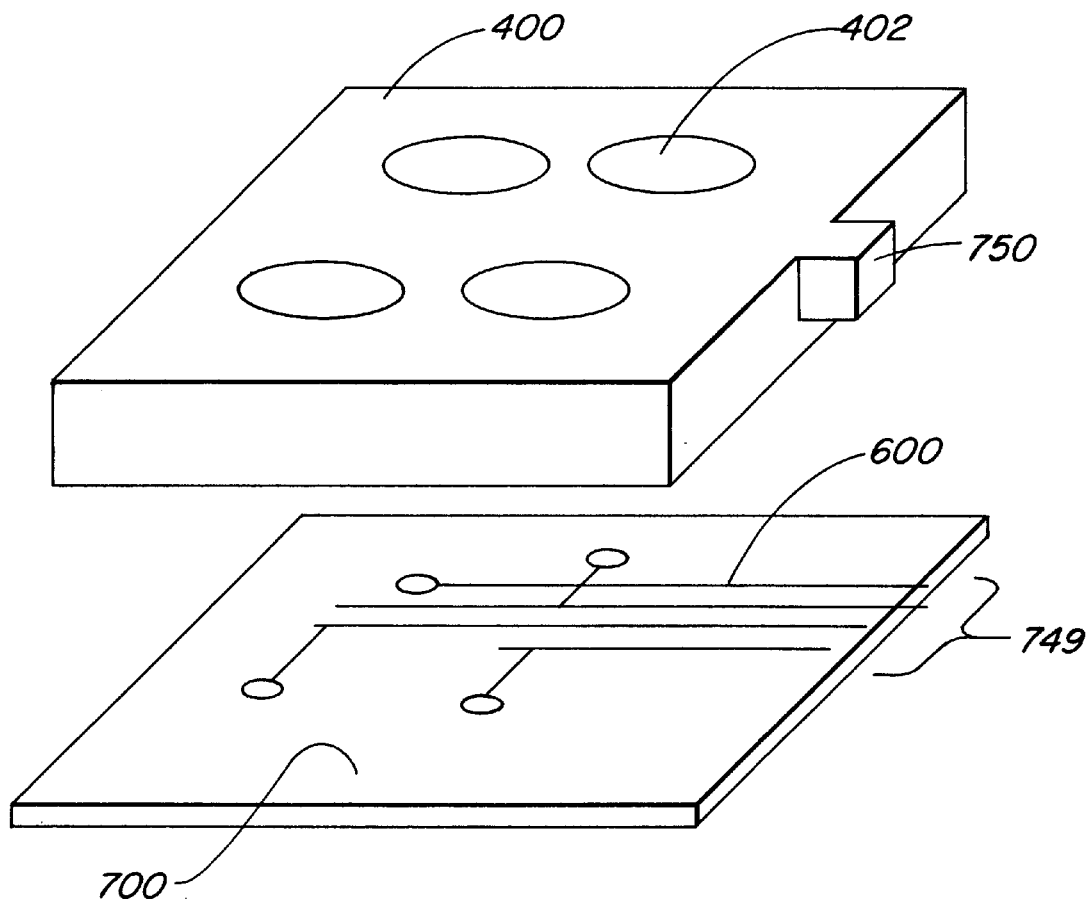
FIG. 3 illustrates the electrical connection housing and the printed circuit board that completes electrical communication between the animal's paws and the signal recording equipment.

Referring now to FIG. 3, and in reference to FIG. 1, the preferred apparatus of the present invention further comprises an electrical connection housing 400 for facile attachment and detachment of the ECG platform (FIG. 1, 104) and electrical transfer of the ECG signals from the animal/pad interface to the signal recording equipment. The housing 400 is generally rectangular in shape and its top surface is designed to physically and electrically mate with the underside of the conductive-pad embedded platform. The housing comprises on its top surface an array of electrical connections 402 or contacts, that detachably mate with the conductive pad terminations 120 of the ECG platform 104. Inside the housing 400, below the top surface of the housing, the electrical connections o 402 are electrically coupled to circuitry means 600 that relay the signal to the ECG recording apparatus 300. In the preferred embodiment, a printed circuit board 700 comprises the circuitry 600 that completes the electrical circuit between each individual electrical connection. The terminations 749 of the circuitry means 600 in the printed circuit board 700 converge towards one end of the housing that is fitted with a jack 750. The jack 750 defines an electrical port that engages circuitry means 600 to enable relaying of the ECG signals from the housing/platform assembly to the recording equipment 300.

Figure 4:
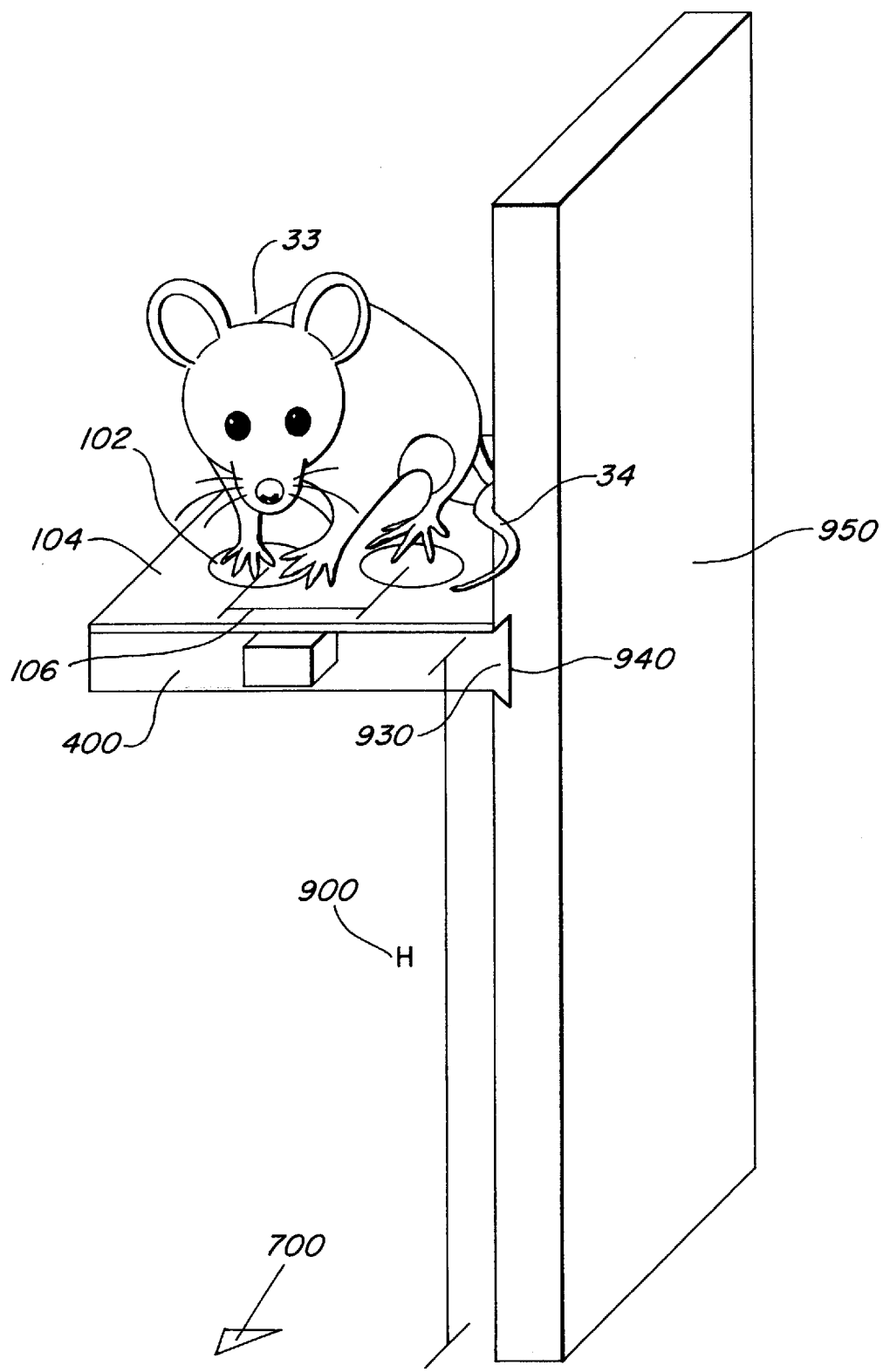
FIG. 4 is a schematic illustrating a mouse standing on the conductive pad-embedded platform assembled to housing, said housing suspended a height above a surface to prevent mouse from alighting to said surface.

Referring now to FIG. 4, the electrical connection housing 400 is disposed generally above any other surface 70 that a mouse 33 might be determined to use as a route of escape from examination. The preferred height 900 of the platform 104 and housing 400 above a surface 70, such as a laboratory bench top or table, is approximately 10 inches, that height 900 found to deter the mouse 33 from attempting to alight from the platform 104 to the neighboring surface 70 and allowing an investigator free access to the mouse and visual appreciation of the mouse's behavior. It is understood that 10 inches is part of a range of heights that accomplish the objectives of preventing the mouse's escape while providing access and visualization of the animal. The height 900 of the platform 104 eliminates the necessity for sides to the platform 104, said sides from which the animal may feel confined or on which the animal might climb.

The electrical connection housing 400 is suspended above the neighboring surface using a suspension means 930,940 that consists of a bracket 940 that is attached to a backstop or wall surface 950 using attachment means such as screws. The bracket defines a track 930 that is interlockingly engaged by track that projects from a side surface of the electrical connection housing. Accordingly, the entire electrical connection housing may be installed simply by mounting bracket 940 at the appropriate height 900 and laterally sliding track 930 into its installed position.

The preferred shape of the pads 102 is circular, although it us understood that other shaped conductive pads would also serve the purpose. The preferred diameter of the pads is 0.4 inches, although it is understood that smaller or bigger pads would also serve the purpose if either smaller or a bigger mouse were to be examined. The preferred spacing between pads 106 is 0.9 inches on center, although it is understood that smaller or bigger spacing would also serve the purpose if either smaller or bigger animals were to be examined.

The preferred apparatus of the present invention further comprises a signal sensing means for detecting the presence of an interpretable ECG signal dependent on cooperative agreement between 3 paws of the animal and 3 unique pads on the platform; and signal recording means responsive to said signal sensing means for triggering acquisition of ECG data from said animal while said animal's paws are in contact with said conductive pads.

Figure 5:
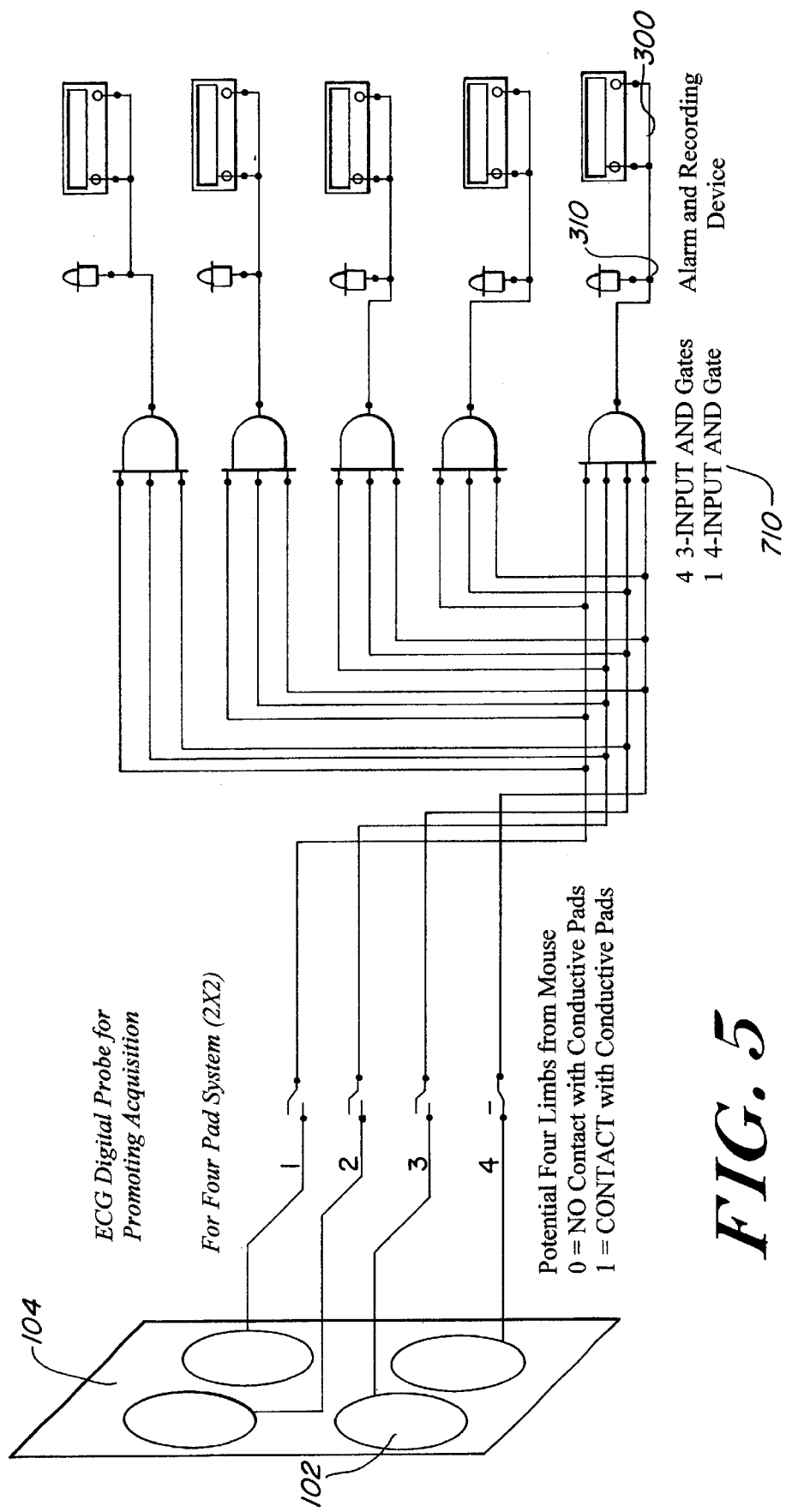
FIG. 5 is an electronic schematic drawing illustrating the signal detection and triggering circuit to activate or deactivate signal recording depending on cooperation between pads and paws.

The circuit schematic of the invention comprising a 2×2 array of conductive pads, for example, is shown in FIG. 5. The circuit 600 takes every combination of three reasonable conductive pads 102 and feeds them as input into a logical AND 710 gate. Reasonable is defined as three conductive pads 102 in electrical contact with three paws without any unusual strain on the animal. For the 2×2 array, there are four reasonable combinations of conductive pads that may generate an electrocardiogram. The logical AND gate is a three input logical gate, with one output. The inputs are classified as either 1's or 0's, whereby 0's signify no animal contact with the conductive pad, and 1's indicate contact with the conductive pad. The possible combinations of input and output are listed below for a specific 2×2 array of conductive pads.

TABLE 1

Logic Combinations of Input and Output for a 2 × 2 Array of Conductive Pads using a 3-Input AND Gate.
Method and apparatis for noninvasively detecting, measuring, recording electrocardiograms in conscious rodents

| Logical Input | Logical Output | Significance |
| --- | --- | --- |
| 000 | 0 | No recordable signal detected |
| 001 | 0 | No recordable signal detected |
| 010 | 0 | No recordable signal detected |
| 100 | 0 | No recordable signal detected |
| 011 | 0 | No recordable signal detected |
| 110 | 0 | No recordable signal detected |
| 101 | 0 | No recordable signal detected |
| 111 | 1 | Recordable Signal Detected |

As the table indicates, when three independent signals are sent into a three input AND gate represented by 111, the output will be a 1, signifying that the gate is activated, and alerts the recording device that the mouse is positioned on pads such as to promote signal acquisition.

The preferred embodiment of the present invention further comprises a signal recording triggering means by which the recording device 300 is alerted that the mouse is positioned on pads 102 sufficiently to acquire the ECG. The output of each AND 710 gate, representing a reasonable 3-point contact configuration of the conscious free moving animal is connected to a signal divider and a recording device 300, and to an alarm system 310, such as a simple red light. The output of the AND gate may serve as a trigger.

When the output generated is a 1, this will trigger an alarm 310 to be activated signifying signal acquisition is possible, and activate a recording device 300 to begin recording the voltage signal generated from the points of contact that originally generated the 1 output from that specific input.

The preferred signal sensing means comprises of continuous circuit sampling for querying the voltage across all of the possible 3-conductive pad configurations that could physiologically render an ECG. The presence of an interpretable ECG will be manifest by the rhythmical presence of a voltage spike (the peak of the "R-wave"). Accordingly, in an alternate embodiment, the signal sensing means comprises a voltmeter and a counter integrated distal to the housing/platform interface. A conventional logic chip is provided for determining whether a predetermined threshold voltage is registered and whether that voltage registration repeats itself a predetermined number of times within a predetermined interval of time, whereupon triggering of acquisition of ECG data from said animal is commenced. In a like fashion, should the voltage fall below threshold voltage and not repeat itself within the predetermined time interval, acquisition of ECG data is terminated.

Figure 6:
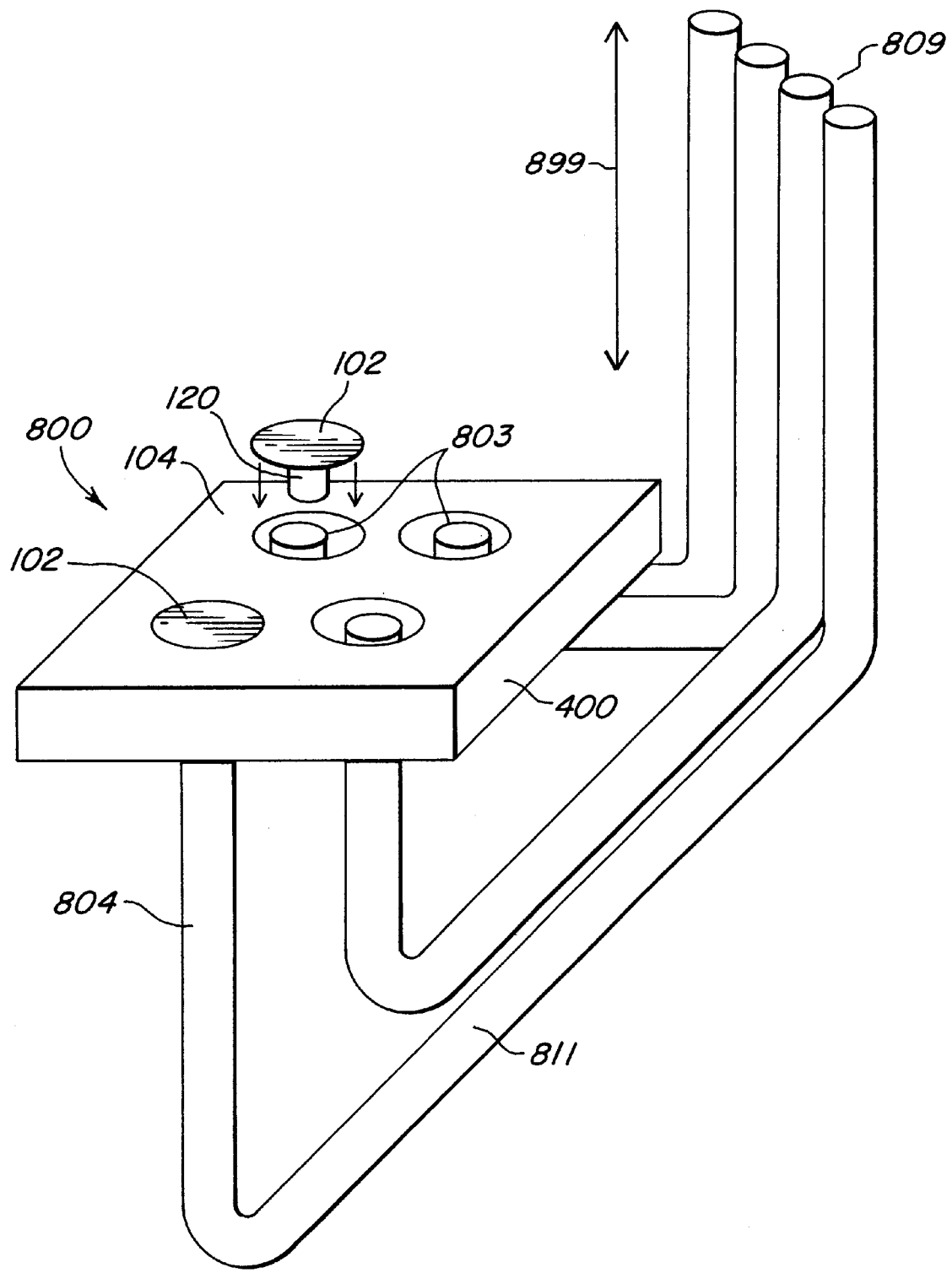
FIG. 6 illustrates the pad and platform apparatus void of any metallic components, and conductive means effected by fluid-filled tubes connected to a reservoir positioned above the platform and housing, said fluid in said tubes in electrical contact with the signal recording equipment.
Figure 8:
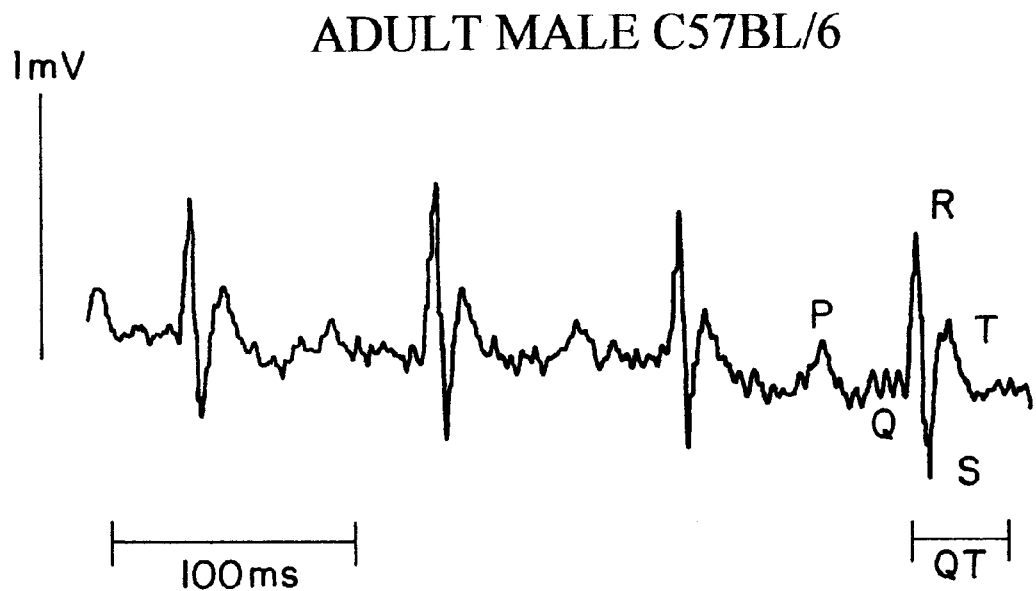
FIG. 8 illustrates ECG waveforms obtained using the present invention in a mouse at baseline (top) and after administered isoproterenol (2.5 $\mu$g/g i.p.).
Figure 8:
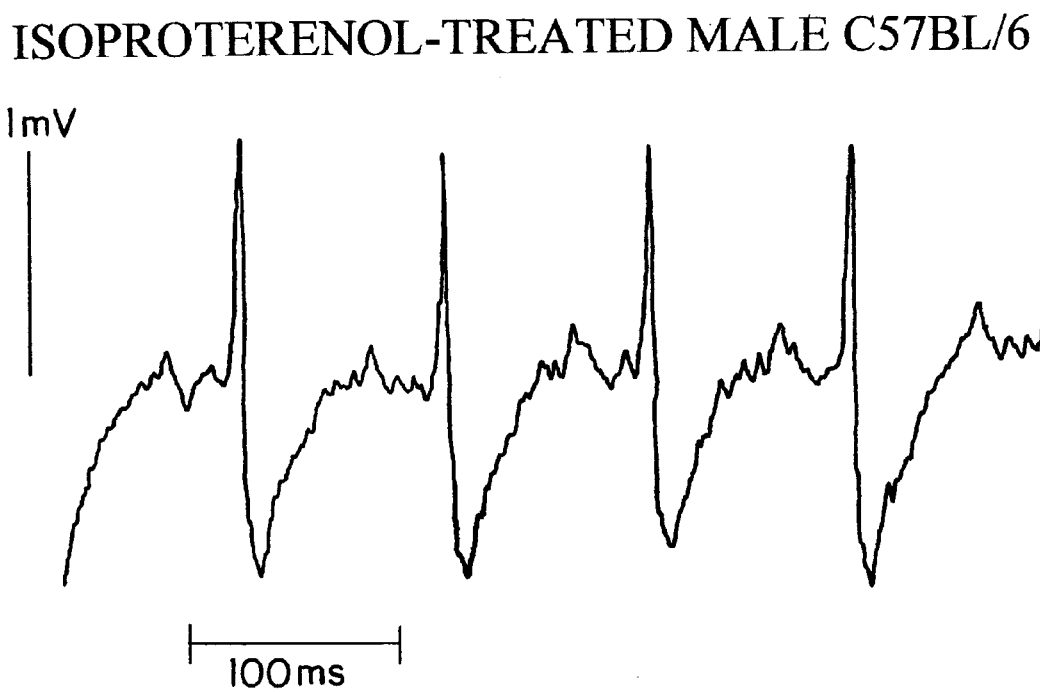

It is also anticipated that the apparatus of the present invention may be installed in locals in which the presence of metallic materials in the apparatus might confound measurement or interpretation of other kinds of signals. For example, researchers interested in using nuclear magnetic resonance to image the animal's organ usually position an anesthetized animal within the bore of the measuring magnet. Gating of image acquisition is difficult unless triggering is enabled by clear demarcations of physiologic events, such as markers on the ECG. Moreover, the anesthetized animal often provides physiological data of limited importance. In FIG. 6, an alternate embodiment device designed for installation in a NMR magnet is illustrated. This device, designated generally 800, operates in the same manner as described for the embodiments of FIGS. 1 and 4. In this embodiment, however, the area of the platform 104 is limited to 6 square inches and no more than 6 conductive pads 102 comprise the platform. On such a platform, a mouse becomes relatively quiescent after a brief acclimation period. In this embodiment, the terminations on the underside of the pads 102 comprise no metallic material. Moreover, the open ends 803 of fluid-filled tubes 804 that extend throughout the housing 400 comprise the electrical circuitry means in the housing. The tubes are filled with a conductive solution 811, such as salt water, that are the electrical circuitry means for relaying the ECG signal to the ECG recording equipment. In one aspect of this embodiment, the jack comprises of fittings to extend the length of tubes 804 by attaching sufficient length of non-metallic tubing to depart the ECG apparatus a sufficient distance such that metallic usage at said distance does not interfere with measurement or interpretation of signals. The tube openings 803 on the housing surface are sized and spaced in accordance with the terminations on the pads 102. The terminations of the pads 120 fit snugly into the tube openings when the pad-embedded platform 104 is positioned on the housing 400. The distal terminations 809 of the tubules are electrically connected to the ECG recording equipment. By extending the tubes to fluid reservoirs a height 899 above the ECG platform 104, the tubes 804 can consistently be repleted with conductive fluid 811. The hydrostatic gradients imposed by the reservoir will not only maintain fluid volume within the tubes, but may also serve to keep the conductive pads 102 moist and conductive. In this embodiment of the invention, there are no metallic materials or components in the housing, the suspension means, platform, or conductive pads.

As seen from the preceding description, a simple method and apparatus for recording ECGs in conscious mice is provided that has demonstrated their ability to provide important physiological information. It is intended that the scope of the invention be defined by the claims appended hereto:

J. D. Meindl et al., "Implantable Telemetry in Biomedical Research;" IEEE Transactions on Biomedical Engineering, vol. BME-31, No. 12, December 1984, pp. 817–823.

Bernward Garthoff, et al., "A New System for the Continuous Direct Recording of Blood Pressure and Heart Rate in the Conscious Rat", Journal of Pharmacological Methods, 1981, pp. 275–278.

Konigsberg Instruments, Inc., "One and Two Channel Telemetry Systems" (brochure), 4 pages.

Thomas A. Patrick, et al., "Telemetry of Left Ventricular Diameter and Pressure Measurements from Unrestrained Animals", Journal of Applied Physiology, August 1974, pp. 276–281.

W. A. Mann, et al., "A Simple Procedure for Direct Blood Pressure Measurements in Conscious Dogs", Laboratory Animal Science, 1986, 8 pages (Reprint).

We claim:

1. A conscious animal electrocardiogram measurement apparatus, comprising:
   a platform mounted a predetermined distance above a neighboring surface, the platform sized and dimensioned to support the animal;
   an array of conductive pads disposed on the platform in a manner enabling passive contact of the array of conductive pads with appendages of the animal;
   a plurality of electrical contacts in electrical communication with the array of conductive pads; and
   a signal recording device;
   wherein the plurality of electrical contacts provide electrical communication between the array of conductive pads and the signal recording device such that the signal recording device can obtain electrocardiogram data from the array of conductive pads.

2. The apparatus of claim 1, wherein the platform is substantially horizontal.

3. The apparatus of claim 1, wherein each conductive pad of the array of conductive pads is spaced to promote the likelihood that at least a minimum number of appendages of the animal make separate contact with a minimum number of conductive pads of the array of conductive pads to produce an electrocardiogram signal.

4. The apparatus of claim 3, wherein the minimum number of appendages is three and the minimum number of conductive pads is three.

5. The apparatus of claim 3, wherein each conductive pad of the array of conductive pads is spaced to decrease the likelihood that more than one appendage of the animal contemporaneously occupies the space of one conductive pad of the array of conductive pads.

6. The apparatus of claim 1, wherein the array of electrical contacts comprises an array of electrical contacts arranged in parallel with the array of conductive pads.

7. The apparatus of claim 1, wherein the signal recording device comprises:
   a sampler for continuously probing conductive pad combinations;
   a signal sensor for detecting when a predetermined number of animal appendages are in contact with a predetermined number of conductive pads of the array of conductive pads;

a signal conditioner for resolving an electric potential of the animal acquired with the predetermined number of conductive pads in contact with the predetermined number of animal appendages into electrocardiogram data;

a signal acquirer for acquiring the electrocardiogram data in a format that promotes quantification and interpretation of the electrocardiogram data; and a signal acquisition trigger responsive to the signal sensor for automatically recording a predetermined quantity of electrocardiogram data.

8. The apparatus of claim 7, wherein the signal conditioner comprises an electrocardiogram amplifier, the signal acquirer comprises an analog to digital converter, and the signal recording device is a computer.

9. The apparatus of claim 7, wherein the signal sensor triggers automatic recording of the electrocardiogram data when the signal sensor senses appropriate contact between the animal and the conductive pads to obtain the electrocardiogram data, and the sensor halts the recording of the electrocardiogram data when the signal sensor does not sense the appropriate contact between the animal and the conductive pads to obtain the electrocardiogram data.

10. The apparatus of claim 1, wherein the platform is sized and dimensioned to allow the animal to move freely about the platform.

11. The apparatus of claim 1, wherein the predetermined distance the platform is mounted above the neighboring surface is determined to hinder the animal from escaping from the platform.

12. The apparatus of claim 11, wherein the predetermined distance the platform is mounted above the neighboring surface is determined to enable observation of the animal and positioning of the animal on the platform.

13. The apparatus of claim 12, wherein the predetermined distance comprises between about six inches and about twelve inches.

14. The apparatus of claim 1, wherein the platform removably engages the array of electrical contacts.

15. The apparatus of claim 1, wherein the platform comprises a liquid absorbing surface for absorbing liquid from the surface of the platform to prevent unwanted electrical connection between the conductive pads.

16. The apparatus of claim 1, wherein the platform comprises an area dimension sufficient to enable a rodent to staid on four legs.

17. The apparatus of claim 16, wherein the platform comprises an area dimension of about six square inches to enable a mouse to stand on four legs.

18. The apparatus of claim 1, wherein the array of conductive pads comprises three conductive pads.

19. The apparatus of claim 1, wherein the platform further comprises a removable sheath that covers a surface of the platform to prevent contamination of the array of conductive pads, wherein removal of the sheath exposes the array of conductive pads for use.

20. The apparatus of claim 1, wherein the plurality of electrical contacts are disposed in a housing mounted relative to the platform.

21. The apparatus of claim 20, wherein the housing comprises a box having a removable wall, which when removed provides access to the plurality of electrical contacts.

22. The apparatus of claim 20, wherein the housing comprises a printed circuit board in electrical communication with the plurality of electrical contacts.

23. The apparatus of claim 22, wherein the printed circuit board is in further electrical communication with a data processing device.

24. The apparatus of claim 21, wherein the housing comprises an electrical connection port removably coupling the array of conductive pads with a signal conditioner and a signal acquirer.

25. The apparatus of claim 24, wherein the housing comprises the signal conditioner.

26. The apparatus of claim 22, wherein the printed circuit board comprises sampling means to rapidly and automatically sample all possible conductive pad combinations for the presence of input from the appendages of the animal.

27. The apparatus of claim 22, wherein the printed circuit board comprises a plurality of electronic multi-input logic gates to detect whether the array of conductive pads are receiving input from the appendages of the animal.

28. The apparatus of claim 20, wherein no metallic material is disposed in the housing and wherein the plurality of electrical contacts are comprised of tubs containing ionic solution in electrical communication with the array of conductive pads.

29. A method of obtaining an electrocardiogram in a conscious animal, comprising:

positioning the animal on a platform comprising an array of conductive pads;

sensing whether appendages of the animal form sufficient contact with conductive pads of the array of conductive pads to enable the gathering of electrocardiogram data;

obtaining the electrocardiogram data from the array of conductive pads; and forming the electrocardiogram based on the electrocardiogram data.

30. The method of claim 29, further comprising recording the electrocardiogram data with a signal recorder in electrical communication with the array of conductive pads.

31. The method of claim 29, further comprising automated activation and termination of obtaining the electrocardiogram data based on sensing whether the appendages of the animal form sufficient contact with the conductive pads of the array of conductive pads to enable the gathering of electrocardiogram data.

32. The method of claim 29, wherein the platform is positioned a predetermined height above a neighbor surface to hinder the animal from escaping from the platform.

33. A conscious animal electrocardiogram measurement apparatus, comprising:

a surface for supporting the animal;

an array of conductive pads disposed on the surface in a manner enabling passive contact of the array of conductive pads with at least one appendage of the animal; and a signal receiving device for receiving electrocardiogram signals from one or more conductive pads of the array of conductive pads.

34. The apparatus of claim 29, wherein the electrocardiogram signals originate when three conductive pads from the array of conductive pads are in passive contact with three appendages of the animal.

35. The apparatus of claim 1, wherein the animal is one of a mouse and a rat.

* * * * *